US00PP12855P2

(12) United States Plant Patent

Cosner et al.

(10) Patent No.: US PP12,855 P2

(45) Date of Patent: Aug. 13, 2002

(54) IMPATIENS PLANT NAMED 'TILIP'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/535,085

(22) Filed: Mar. 23, 2000

(30) Foreign Application Priority Data

Mar. 30, 1999 (CA) ..... 99-1616

(51) Int. Cl.[7] ..... A01H 5/00

(52) U.S. Cl. ..... Plt./317

(58) Field of Search ..... Plt./317

(56) References Cited

U.S. PATENT DOCUMENTS

PP9,616 P * 7/1996 Leue ..... Plt./317

OTHER PUBLICATIONS

UPOV ROM GTITM Computer Database, GTI JOUVE Retrieval software, 2001/02, citation for 'TiLip'.*

* cited by examiner

*Primary Examiner*—Bruce R. Campell

*Assistant Examiner*—Anne Marie Grünberg

(74) *Attorney, Agent, or Firm*—Ganz Law, P.C.; Bradley M. Ganz, Esq.

(57) ABSTRACT

A new and distinct cultivar of '*Impatiens walleriana*' plant named 'TiLip,' characterized by large light pink fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as '*Impatiens walleriana*,' and by the cultivar name 'TiLip'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The closest known cultivar of prior art is named 'Pink Ruffles,' subject of U.S. Plant Pat. No. 9,616.

COMPARISON

The impatiens plant of the present invention differs from prior plants, namely 'Pink Ruffles' in at least the following ways:

1. The plant of the present invention has been shown to be more compact than 'Pink Ruffles;'

2. The plant of the present invention has been shown to have shorter internodes than those of 'Pink Ruffles;'

3. The present cultivars have also been shown to have stronger peduncles and pedicels than 'Pink Ruffles;'

4. The plant of the present invention has been shown to be more rain tolerant than 'Pink Ruffles;' and 5. the flowers of the present invention have been shown to have lighter colored flowers than 'Pink Ruffles'.

These and other characteristics will be apparent to persons skilled in the art.

BACKGROUND—DISCOVERY AND PARENTAGE

The present cultivar was developed by standard cross-pollination. Its seed parent is a semi-double impatiens plant with salmon flowers. This plant was designated 'B-9X-4726' (unpatented) in the inventors' controlled breeding program. The pollen parent is a semi-double impatiens plant with white flowers. This plant was designated 'B-9X-113' (unpatented) in the inventors' controlled breeding program. The cross was made in the inventors' controlled breeding program, and the first asexual reproduction was made at Broadbent, Oreg. Successive asexually reproduced generations have shown the present invention to be stable. Each asexually reproduced generation has been accomplished using cuttings of lateral stems with leaves.

The traits of the cultivar of the present invention that have been observed in each successive generation of asexual reproduction and which are unique are the large light pink fully double flowers, flowers that are positioned above or beyond the foliage, good heat tolerance, dark green foliage and mounded, freely branching and dense plant habit.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of 2 feed, one leach. Plants started in the last week of June and finished in late September. Light levels were from 4,000 to 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. There may be variations between the colors in the photograph and the colors in the following description due to light reflectance, or the amount of blue or red light captured in the film. If such variations occur, the written description shall control.

Parentage: The new cultivar was developed by standard cross-pollination. As noted above, its seed parent was a semi-double with salmon flowers; its pollen parent was a semi-double with white-colored flowers.

Propagation:

*Type cutting.*—Lateral stems with leaves were the cuttings used for asexual reproduction.

*Time to initiate roots.*—Approximately 7 to 14 days at 72° F. soil temperature.

Appearance and form of plant:

*Plant form and habit.*—Mounded and upright vase, with a medium vigorous, dense and bushy growing habit. A free-branching habit.

*Plant size.*—Height is about 22 cm and width is about 35 cm.

*Rooting description.*—The rooting description is characterized by numerous, fibrous and well-branched roots.

*Branching habit.*—Plants are self-branching. Stems are strong and freely produced. The number of stems depends upon cultural practices, age of stems used as cuttings and the number of growth buds present on the cutting when stuck.

*Stems.*—Diameter is about 0.5 cm. Internode length is about 2.5 cm. Color is close to 146B marked with darker spots close to 178A.

*Foliage.*—Leaves are simple, generally symmetrical, abundant, alternate and flat. Shape is ovate with attenuate base, acuminate apex, and crenate margin. Texture is smooth and satiny.

*Foliage size.*—Size of the largest leaves is about 5 cm in length, and 4.5 cm in width.

*Foliage color.*—Adaxial color is darker than 146A, venation color 146A; abaxial color is 146B with venation color 146A.

*Petioles.*—Petiole shape is half round with a flat upper surface measuring about 2 mm wide, about 1.5 mm in depth, and about 2 cm in length. Color on the top is 146C with tiny hard to determine markings due to their small size which appear close to 178A. Color on bottom surface is 146D.

*Flower size.*—Largest flowers have a diameter of about 5 cm, and depth of about 1.5 cm.

*Flower texture.*—The flower texture is smooth and satiny.

*Flower count.*—Flowers per stem usually number about 12 per branch from visible buds to open flowers at any time during the flowering period.

*Natural flowering season.*—Year around under greenhouse conditions, and the frost-free period from spring through fall outdoors. Flowers are continuously produced throughout the flowering season.

*Duration of flower.*—About four to seven days.

*Time to flower.*—About six weeks from a rooted cutting.

*Buds.*—Ovate shape with length of about 1.2 cm, width of about 0.8 cm and depth of about 1 cm. Color of top is 145A and bottom color is 145B.

*Petal size and shape.*—Shape is obovate to exaggerated obovate, attentuate to cuneate base, entire margin, obtuse to retuse apex. Usually two petals fused at base comprise the largest petals, each being about 1.8 cm wide and 2.3 cm long.

*Petal color.*—Adaxial is 62B to 62C with darker veining close to 62A and adaxial base close to 67B. Abaxial color is 65C.

*Petal count.*—Numerous, usually 25 or more.

*Spur.*—Shape is acicular tapering tube, usually curved. Color at apex is 177C and 194B at base with markings of 178B. Length is about 3 cm and width is about 2 mm.

*Calyx.*—The calyx consists of a single sepal. The sepal shape is ovate with truncate to cordate base, and acuminate apex, entire margin. Length is about 1.2 cm and width is about 0.8 cm. Adaxial color is 142D with a base spot close to 66C; abaxial color is 142C.

*Peduncles.*—Length is about 2 cm and diameter is about 2 mm. Color is 146B with hard to determine reddish markings appearing close to 178B.

*Pedicels.*—Length is about 1.8 cm and diameter is about 1 mm, generally numbering from 2 or 3 per peduncle, color is 146C with tiny markings the color of which is hard to determine due to their small size but which appear close to 178A.

*Reproductive organs.*—The plants of the new cultivar are both male and female sterile. No reproductive organs have been found to exist.

*Disease resistance.*—The instant plant has shown to have good resistance to botrytis.

*Rooting ability.*—Easy, no hormones needed.

*Cold/heat resistance.*—This cultivar has flowered continuously in temperatures of 85° F. to 95° F.

*Dampness resistance.*—The peduncles of 'Pink Ruffles' are weaker than the peduncles of the instant plant. In the rain, the flowers of 'Pink Ruffles' droop, or hang down much more than the flowers of the instant plant. This comparison was made at Broadbent Oreg.

What is claimed:

1. A new and distinct cultivar of '*Impatiens walleriana*' plant, as illustrated and as described herein.

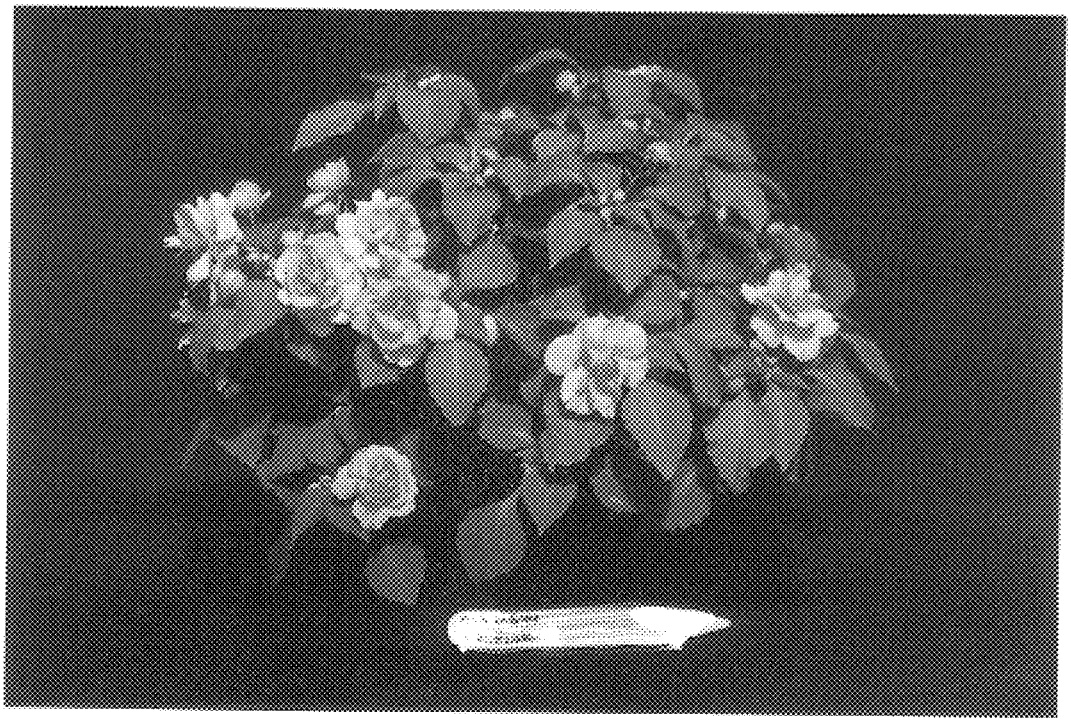

* * * * *